(12) United States Patent
Liu et al.

(10) Patent No.: US 9,798,930 B2
(45) Date of Patent: Oct. 24, 2017

(54) DETERMINING ELONGATION OF ELASTIC BANDAGE

(71) Applicant: 3M INNOVATIVE PROPERTIES COMPANY, St. Paul, MN (US)

(72) Inventors: Junkang J. Liu, Woodbury, MN (US); Timothy M. Dietz, Mendota Heights, MN (US)

(73) Assignee: 3M Innovative Properties Company, St. Paul, MN (US)

(*) Notice: Subject to any disclaimer, the term of this patent is extended or adjusted under 35 U.S.C. 154(b) by 129 days.

(21) Appl. No.: 14/406,812

(22) PCT Filed: Jul. 3, 2013

(86) PCT No.: PCT/US2013/049220
§ 371 (c)(1),
(2) Date: Dec. 10, 2014

(87) PCT Pub. No.: WO2014/014672
PCT Pub. Date: Jan. 23, 2014

(65) Prior Publication Data
US 2015/0154451 A1    Jun. 4, 2015

Related U.S. Application Data

(60) Provisional application No. 61/673,507, filed on Jul. 19, 2012.

(51) Int. Cl.
*G06K 9/00* (2006.01)
*G06T 7/60* (2017.01)
(Continued)

(52) U.S. Cl.
CPC ........ *G06K 9/00671* (2013.01); *G01B 11/165* (2013.01); *G01L 1/24* (2013.01);
(Continued)

(58) Field of Classification Search
None
See application file for complete search history.

(56) References Cited

U.S. PATENT DOCUMENTS 3,575,782 A    4/1971  Hansen
3,613,679 A   10/1971  Bijou
(Continued)

FOREIGN PATENT DOCUMENTS

CN    201631447 U    11/2010
EP       0475811       3/1992
(Continued)

OTHER PUBLICATIONS

Schuren et al., "The efficacy of Laplace's equation in calculating bandage pressure in venous leg ulcers", Wounds UK, 2008, vol. 4 No. 2, pp. 38-47.*

(Continued)

*Primary Examiner* — Matthew Bella
*Assistant Examiner* — Jose M Torres

(57) ABSTRACT

The present invention is directed to new methods of determining elongation, tension and applied pressure of elastic bandages comprising tension indicators. In one embodiment, a computer-implemented method of detecting elongation of an elastic bandage (e.g. on a mobile computing device having a processor and graphical user interface) is described. The method comprises receiving image data that includes a digital photograph of an elongated tension indicator of an elastic bandage; analyzing the image data to determine elongation of the elastic bandage by comparing geometric features of the elongated tension indicator to model geometric features that define a predetermined elongation state (such as an unelongated state); and providing output indicia associated with the determined elongation. Also described are various articles, some of which are intermediate articles of the methods described herein. Such (Continued)

articles include non-transient computer readable medium, a three-dimensional member comprising at least one layer of certain elastic bandages. In one embodiment, the elastic bandage comprises a tension indicator and a computer readable code.

19 Claims, 10 Drawing Sheets

(51) Int. Cl.
  *G06K 9/22* (2006.01)
  *G01L 5/04* (2006.01)
  *G01B 11/16* (2006.01)
  *G01L 1/24* (2006.01)
  *G06T 7/00* (2017.01)
  *G06T 7/246* (2017.01)
  *A61F 13/08* (2006.01)

(52) U.S. Cl.
  CPC .............. *G01L 5/045* (2013.01); *G01L 5/047* (2013.01); *G06K 9/228* (2013.01); *G06T 7/0014* (2013.01); *G06T 7/251* (2017.01); *G06T 7/60* (2013.01); *A61F 13/08* (2013.01); *G06T 2200/24* (2013.01); *G06T 2207/10004* (2013.01); *G06T 2207/30004* (2013.01); *G06T 2207/30208* (2013.01)

(56) References Cited

U.S. PATENT DOCUMENTS

| | | | |
|---|---|---|---|
| 4,984,584 A | 1/1991 | Hansen | |
| 5,445,604 A | 8/1995 | Lang | |
| 6,050,967 A * | 4/2000 | Walker | A61F 13/00059 602/75 |
| 6,156,424 A | 12/2000 | Taylor | |
| 6,338,723 B1 | 1/2002 | Carpenter | |
| 6,432,074 B1 * | 8/2002 | Ager | A61F 13/00059 602/75 |
| 7,260,999 B2 | 8/2007 | Divigalpitiya et al. | |
| 7,458,234 B2 | 12/2008 | Yamamura | |
| 7,477,995 B2 * | 1/2009 | Hovis | G01D 5/34707 356/32 |
| 7,854,716 B2 | 12/2010 | Schuren | |
| 7,956,233 B2 | 6/2011 | Lecomte | |
| 8,372,024 B1 * | 2/2013 | Henderson | A61F 13/0273 602/53 |
| 2004/0036853 A1 | 2/2004 | Vachon | |
| 2005/0025937 A1 | 2/2005 | Maki | |
| 2005/0049741 A1 * | 3/2005 | Dias | D04B 7/32 700/141 |
| 2007/0055537 A1 * | 3/2007 | Bassez | A61F 5/01 705/2 |
| 2007/0209447 A1 | 9/2007 | Christ, Jr. | |
| 2009/0316965 A1 | 12/2009 | Mailling | |
| 2011/0183712 A1 | 7/2011 | Eckstein | |
| 2012/0164615 A1 * | 6/2012 | Al Khaburi | G09B 23/30 434/267 |
| 2013/0131565 A1 * | 5/2013 | Dallafior | A61F 5/01 602/5 |

FOREIGN PATENT DOCUMENTS

| | | |
|---|---|---|
| EP | 1731096 | 12/2006 |
| EP | 2220996 | 8/2010 |
| GB | 2445760 | 7/2008 |
| JP | 4194685 | 11/1990 |
| JP | 3040425 | 2/1991 |
| JP | 3147797 | 6/1991 |
| JP | H 08-075627 | 3/1996 |
| WO | WO 2006-103422 | 10/2006 |
| WO | WO 2008/006227 | 1/2008 |

OTHER PUBLICATIONS

Thomas, "The Use of Laplace Equation in the Calculation of Sub-bandage pressure", EMWA Journal 2003, vol. 3 No. 1, pp. 21-23.*
Supplementary EP Search Report, Application No. 13820155, dated Jun. 27, 2016.
K2 Two-Layer Compression Bandaging System, URGO Laboratories, 2 pages, 2015.
MedexSupply, J&J Dyna-Flex Multi-Layer Compression System Kit, 5"×9", [online] [retrieved from internet on Jun. 25, 2012], URL < http: //www.medexsupply.com/printerfriendly. php ?products id=72682>, 2 pages.
Setopress, P.E.C. Medium/High Compression Bandage; 1 page, 2015.
Smith & Nephew, Instructions for use, Proguide, "Vari-Stretch Compression Bandage System", Smith & Nephew, [retrieved from internet on Jun. 25, 2012], URL < http: //global.smith-nephew.com/us/PROGUIDE 21961_PROGUIDE_21963 .htm>, 4 pages.
"SurePress High Compression Bandage"; ConvaTec Inc., 2010, 1 page.
Thomas, "World Wide Wounds, Compression Bandaging in the Treatment of Venous Leg Ulcers", Bridgend District and NHS Trust, Bridgend, [online] Aug. 12, 1997, [retrieved from the internet on Jun. 25, 2012], URL <http://www.worldwidewounds.com/1997/september/Thomas-Bandaging/bandage-paper.html>, 16 pages.
International Search Report for PCT International Application No. PCT/US13/49220 dated Dec. 6, 2013, 4 pages.
2008 (WUWHS. Principles of Best Practice: compression in venous leg ulcers. A consensus document. 2008; MEP Ltd, 5 London) pp. 1-10.
Supplementary Partial European Search Report EP 13 82 0155 Feb. 5, 2016, 4 pages.

* cited by examiner

DETERMINING ELONGATION OF ELASTIC BANDAGE

CROSS REFERENCE TO RELATED APPLICATIONS

This application is a national stage filing under 35 U.S.C. 371 of PCT/US2013, filed Jul. 3, 2013, which claims priority to U.S. Provisional Application No. 61/673,507, filed Jul. 19, 2012, the disclosure of which is incorporated by reference in their entirety herein.

BACKGROUND

Compression bandages are known for use in the treatment of oedema and other venous and lymphatic disorders, e.g., of the lower limbs. An area where compression bandages are considered particularly useful is in the management and treatment of chronic wounds, such as venous leg ulcers. Achieving optimum pressure when applying compression to (e.g. leg) ulcer patients creates challenges for the clinician.

U.S. Pat. No. 3,613,679 describes an elastic bandage with a tension indicator. A series of figures forming an overall pattern is applied to the surface of an elastic bandage. When the bandage is stretched, the contours of the figures and/or their position relative to each other are altered. The degree of such alteration is an indication of the amount of tension existing in the bandage and the pressure applied by the bandage.

U.S. Pat. No. 7,956,233 refers to such tension indicator as a calibration means. As described beginning at col. 8, lines 20, "This calibration means may be visual, such as for example a set of regularly spaced pictograms printed on the bandage, or produced using a calibration system, such as for example a stencil, by the care staff who are provided with information on the recommended stretch on application. This type of stencil or the explanations necessary to manufacture it may be incorporated in a kit that includes the two support bandages that form the compression system or a selection of support bandages that allow various suitable compression systems to be produced. The principle of calibration using a stencil is the following. The stencil is generally produced by means of a cardboard sheet in which an opening has been cut that may have, for example, an ellipsoidal or rectangular shape, allowing, as will be understood, a pictogram of the same shape to be produced on the bandage. The transformation of these pictograms into circles or squares under the effect of stretching the bandage thus allows the latter to be calibrated. This principle is described, for example, in U.S. Pat. No. 3,613,679. The rectangular shape, which is easiest to cut in a cardboard sheet, is preferably used. The length and the width of the rectangle are mathematically determined depending on the stretch at which the bandage is intended to be applied. Hence if E is the stretch of the bandage on application and L the length of the rectangle that will be parallel in the weft direction of the bandage (i.e. perpendicular to the length direction of the bandage), the width L of the rectangle will be L/(1+E'). For example, to calibrate a bandage that is intended to be applied with a 55% stretch, a rectangle having a length of 4 cm and a width of 4/(1+0.55) or 2.58 cm will be used. To calibrate the bandage, rectangles of 4 cm length and 2.58 cm width are cut into a cardboard stencil. This stencil is positioned on the flat, unstretched bandage and the outline of this rectangle is drawn on the bandage, for example using a felt-tip pen."

Various bandages with tension indicators are commercially available including for example ProGuide®, available from Smith & Nephew, Setopress®, available from Molylncke, Surepress®, available from Convatek, and K-Two®, available from Urgo Medical. In a study in 2008 (WUWHS. Principles of Best Practice: compression in venous leg ulcers. A consensus document. 2008; MEP Ltd, London) it was shown that compression bandages with visual indicators were applied more accurately than bandages without indicators. Some of these types of bandages are also self-adherent, which means they stay in place more easily.

SUMMARY

The present invention is directed to new methods of determining elongation, tension and applied pressure of elastic bandages comprising tension indicators.

In one embodiment, a computer-implemented method of detecting elongation of an elastic bandage (e.g. on a mobile computing device having a processor and graphical user interface) is described. The method comprises receiving image data that includes a digital photograph of an elongated tension indicator of an elastic bandage; analyzing the image data to determine elongation of the elastic bandage by comparing geometric features of the elongated tension indicator to model geometric features that define a predetermined elongation state (such as an unelongated state); and providing output indicia associated with the determined elongation.

In another embodiment, a computer-implemented method of detecting applied pressure of an elastic bandage is described. The method comprises receiving image data that includes a digital photograph of an elongated tension indicator of an elastic bandage applied to a three-dimensional member; analyzing the image data to determine the elongation of the elastic bandage is determined by comparing geometric features of the elongated tension indicator to model geometric features that define a predetermined elongation state; utilizing the Laplace equation to determine the applied pressure; and providing indicia associated with applied pressure.

The Laplace Equation is as follows: Applied Pressure (mmHg)=(TN×4360)/CW; wherein T is tension in kgf, N is number of applied layers, C is circumference in cm of the three-dimensional member, and W is width of the bandage in cm.

The tension is determined from the elongation of the elastic bandage and stress-strain indicia. The additional input variables for utilizing the Laplace equation (e.g. stress-strain indicia, N, C, and W) can be obtained in various manners. The circumference of the three-dimensional member and width of the bandage can typically be determined from analysis of the digital photograph. The stress-strain indicia is typically provided in a reference library associated with a computer readable code associated with the elastic bandage. Further, the number of applied layer is typically separately received by entering such value via a touchscreen or keyboard and in some embodiments in combination with the extent of overlap of the applied elastic bandage.

In other embodiments, methods of detecting elongation, tension, applied pressure etc. are described with respond to the steps conducted by the user of such computer-implemented method, i.e. whereas the steps of receiving and providing are reversed. The user may be a healthcare practitioner that is applying or verifying the application of a compression bandage. The user may also be a patient or caregiver that is not a healthcare professional. For example in one embodiment, a computer-implemented method of detecting elongation of an elastic bandage is described comprising providing image data that includes a digital photograph of an elongated tension indicator of an elastic bandage; analyzing the image data or transmitting the image data to determine the elongation of the elastic bandage by comparing geometric features of the elongated tension indicator to model geometric features that define a predetermined elongation state; and providing output indicia associated with the determined elongation.

Also described are various articles, some of which are intermediate articles of the methods described herein. Such articles include non-transient computer readable medium, a three-dimensional member comprising at least one layer of certain elastic bandages. In one embodiment, the elastic bandage comprises a tension indicator and a computer readable code. For example, a computer readable code may be embedded in the tension indicator.

In each of the above flow charts, "unelongated tension indicator" is described as an illustrative predetermined elongation state. Such methods can utilize any predetermined elongation state and are not limited to the use of an unelongated state as the predetermined elongation state.

DETAILED DESCRIPTION

Figure 1:
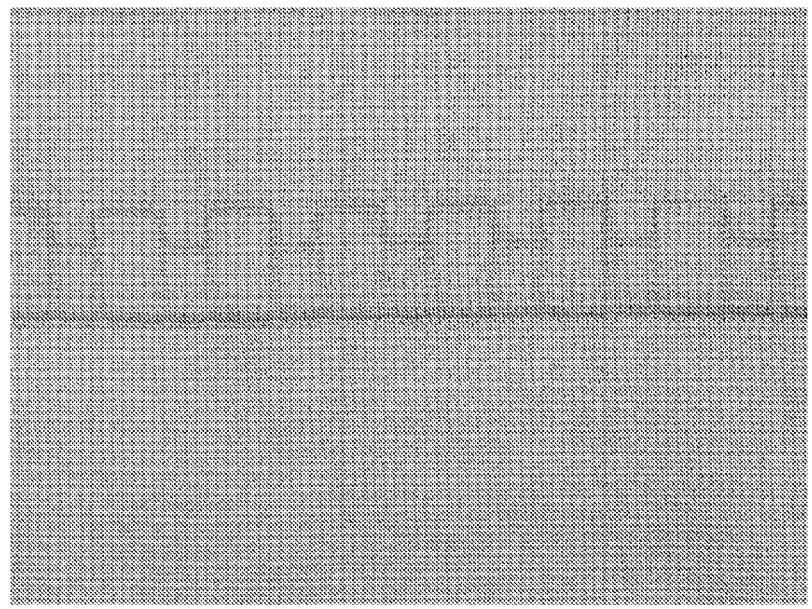
FIG. 1 is a digital photograph of an unelongated tension indicator.

The methods described herein utilize an elastic bandage comprising a tension indicator. Various bandages with tension indicators are known. A tension indicator is generally a series of figures forming an overall repeating pattern applied to the (e.g. outer) surface of an elastic bandage. The figure or figures of the tension indicator may be of any shape including for examples rectangles, squares, circles or elipses. Regardless of the shape or arrangement, the tension indicator provides a visual indication of varying amounts of elongation. When the bandage is stretched, the shape or contours of the figures and/or their position relative to each other are altered. The change in shape and/or position of the tension indicator figures is an indication of the amount the bandage is elongated. For example, one illustrative tension indicator of a compression bandage available from Convatek under the trade designation Surepress® is depicted in FIG. 1. According to the compression bandage application instructions included with the bandage, for a "normal limb (18-26 cm ankle) the bandage should be stretched such that the small boxes become square. For a "large" limb (over 26 cm), the bandage should be stretched such that the large boxes become square.

In some embodiments, the tension indication may comprise a repeating pattern of a set of geometric tension indicator wherein the set comprises at least two, three or more distinct marking, each distinct marking associated with a different elongation of the bandage. The repeat interval of the repeating pattern is typically no greater than about half the circumference of the three-dimensional member to which the elastic bandage is intended to be applied. In some embodiments, the repeat interval is no greater than about 10 cm, 9 cm, 8 cm, 7 cm, 6 cm or 5 cm.

By distinct it is meant that the markings can be distinguished from each other. In some embodiments, the distinct markings may comprise the same or similar shaped figures, the figures being of different sizes. The tension indicator of FIG. 1 comprising two alternating rectangles of different sizes is illustrative of this embodiment. In some embodiments, the distinct markings may comprise differently shaped figures, such as a combination of elipses and rectangles.

The size of the figures of the tension indicator can vary. Typically the smallest dimension of the figures is at least 3 to 5 mm and typically no greater than about 20 mm.

Figure 2:
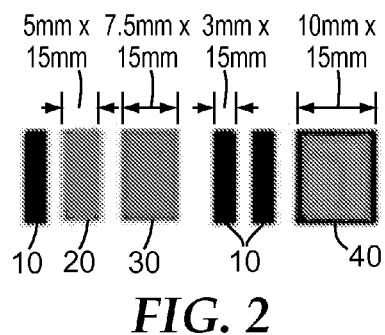
FIG. 2 is another embodied tension indicator for an elastic bandage.

The distinct marking may also comprise similar or different shaped figures having different colors. For example, FIG. 2 depicts an interval of a tension indicator comprising 4 rectangular bars having the same height (e.g. 15 mm) a different width. Preferably, each bar of a different width also has a different color. For example, bars 10, having a width of about 3 mm, may be black; bar 20, having a width of 5 mm, may be red; bar 30, having a width of 7.5 mm, may be blue; and bar 40, having a width of about 152 mm may be green.

When bars 10 are stretched from 3 mm to 15 mm, such that bars 10 form a 15 mm×15 mm square, the elastic bandage has been elongated 400% (final dimension−initial dimension/initial dimension)×100%. In the same manner, stretching bar 20 from 5 mm to 15 mm indicates an elongation of 200%; stretching bar 30 from 7.5 mm to 15 mm indicates an elongation of 100%; and stretching bar 40 from 10 mm to 15 mm indicates an elongation of 50%.

The tension indicator code of FIG. 2 may be about actual size for a 4 inch wide elastic bandage. Alternatively, such code may be reduced or enlarged in size provided the scale is maintained.

The color of the tension indicator is preferably of sufficient contrast as compared to the elastic bandage material that it is readily discernible from the digital photograph thereof. Tension indicators having figures of filled color(s)

rather than the outline of a figure can also be favored in order that the tension indicator is readily discernible.

In some embodiments, such as depicted in FIG. 1, the elastic bandage comprises a continuous or intermittent marking in a central portion (relative to the width of the bandage) that is parallel to the length of the elastic bandage. This feature can serve as guide for the extent of overlap. For example, in the case of the elastic bandage depicted in FIG. 1, such parallel line is in the middle. When such elastic bandage is applied to a three-dimensional member, a longitudinal edge (parallel to the direction of stretch) of the overlapping layer of the bandage is positioned such that it is aligned with the middle marking and the layer is overlapped by 50%. Other target overlaps may be desired for other elastic bandages or certain end uses. Thus, such continuous or intermittent marking in the central portion of the elastic bandage may be positioned at other locations to serve as a guide for any amount of overlap generally ranging from about 25% to 30% to 50% overlap. It is appreciated that a 25% guide can also be used as a guide for 75% overlap. Although the overlap guide marking may be integrated with the tension indicator as in the case of the elastic bandage depicted in FIG. 1, the overlap guide marking can be a separate marking than the tension indicator. Further the elastic bandage may comprise more than one overlap guide marking.

Figure 3:
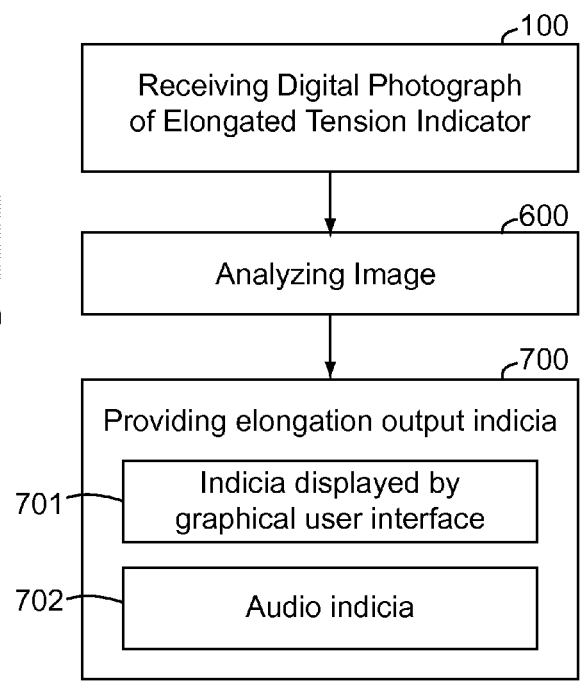
FIG. 3 is a flow chart of an embodied method of determining elongation of an elastic bandage.

Presently described are computer-implemented methods of detecting elongation, tension and applied pressure of an elastic bandage. In favored embodiment, such methods utilize a mobile computing device having a processor and a graphical user interface, commonly referred to as a "Smartphone". The Smartphone is typically utilized at least for the purpose of providing a digital photograph of an elongated tension indicator of an elastic bandage (applied to a three-dimensional member) to the computer program and for the purpose of receiving output indicia associated with the elongation or applied pressure of the elastic bandage calculated by the program. Thus, the tension indicator marking is not only used as a visual indicator by a clinician applying the elastic bandage, but also utilized by the computer program in the form of digital indicia. When the computer program is within the Smartphone, the processor of the Smartphone may also be utilized for the purpose of analyzing the image data to determine elongation and/or calculating the applied pressure. However, in other embodiments, a remote serve may conduct the steps of analyzing the image data to determine elongation and/or calculating the applied pressure. Regardless of whether a Smartphone or remote server is conducting the analysis, with reference to FIG. 3, the method generally comprises receiving image data that includes a digital photograph of an elongated tension indicator of an elastic bandage 100, analyzing the image data (with a processor of a mobile-computing device or remote server) to determine elongation of the elastic bandage 600 by comparing geometric features of the elongated tension indicator to model geometric features that define a predetermined elongation state, and providing output indicia associated with the determined elongation 700. The output indicia can be displayed by the graphical interface 701 or can be audio indicia 702.

Various output indicia may be provided by the computer program. In some embodiments, the output indicia may be pass/fail indicia. For example, the output indicia may comprise a "green light" when the elongation or pressure is within a specified target range and a "red light" when outside the target range. The pass/fail indicia may also be different sounds. In another embodiment, the output indicia may be a numerical value, calculated from the analysis. In yet other embodiments, the output indicia may include displayed or audio instructions concerning the elastic bandage application technique.

Figure 4:
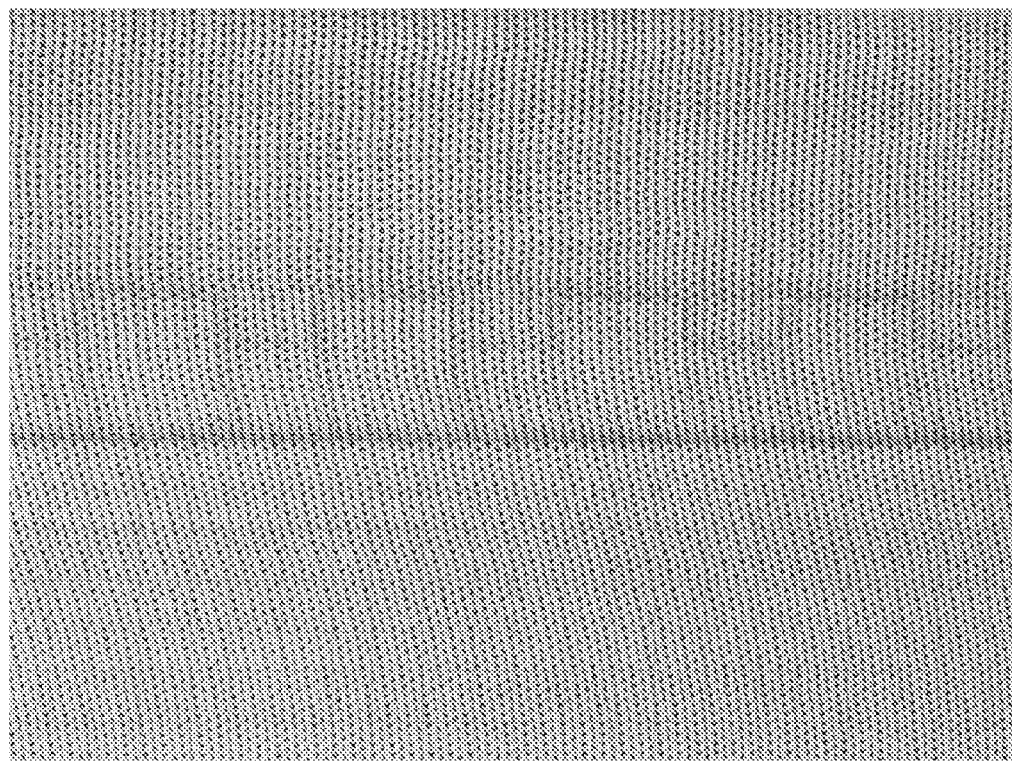
FIG. 4 is a digital photograph of an elongated tension indicator.

FIG. 4 depicts a digital photograph of an illustrative elongated tension indicator. During analysis the computer program of the Smartphone computer application or remote server compares the geometric features of the elongated tension indicator to model geometric features that define a predetermined elongation state. The term geometric refers to the ordinary meaning of the mathematics of the properties, measurement, and relationships of point, lines, angles, and surfaces. The term "feature" refers to any distinct part or the overall appearance of all the parts of the figure or figures of the tension indicator. In typical embodiments, the predetermined elongation state of the tension indicator is the unelongated state of the tension indicator. However, since there is typically a linear relationship between the change in shape and/or position of the tension indicator figures and the amount of stretch, the predetermined elongation state of the tension indicator can be any known elongation state.

In one embodiment, the predetermined (e.g. unelongated) elongation state is preloaded and stored in the computer program of the Smartphone or remote server. The computer program computes the difference between the elongated and predetermined (e.g. unelongated) elongation state.

Figure 5:
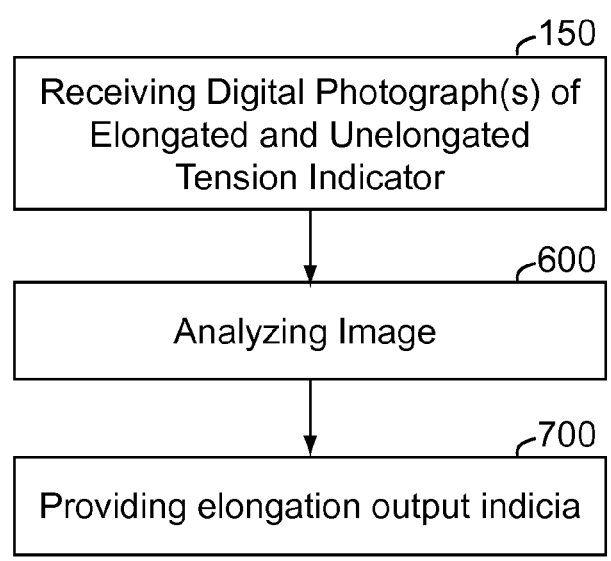
FIG. 5 is a flow chart of an embodied method of determining elongation of an elastic bandage by utilizing a digital photograph of an unelongated tension indicator for the purpose of defining a predetermined (unelongated) elongation state.

With reference to FIG. 5, in another embodiment, the predetermined elongation state is the unelongated tension indicator and the unelongated tension indicator is also received 150 by the computer application program as image date that includes a digital photograph of the elongated tension indicator, such as depicted in FIG. 4. The digital photograph of the elongated tension indicator can be the same or a second (separate) digital photograph as the digital photograph that comprises the elongated tension indicator.

Figure 6:
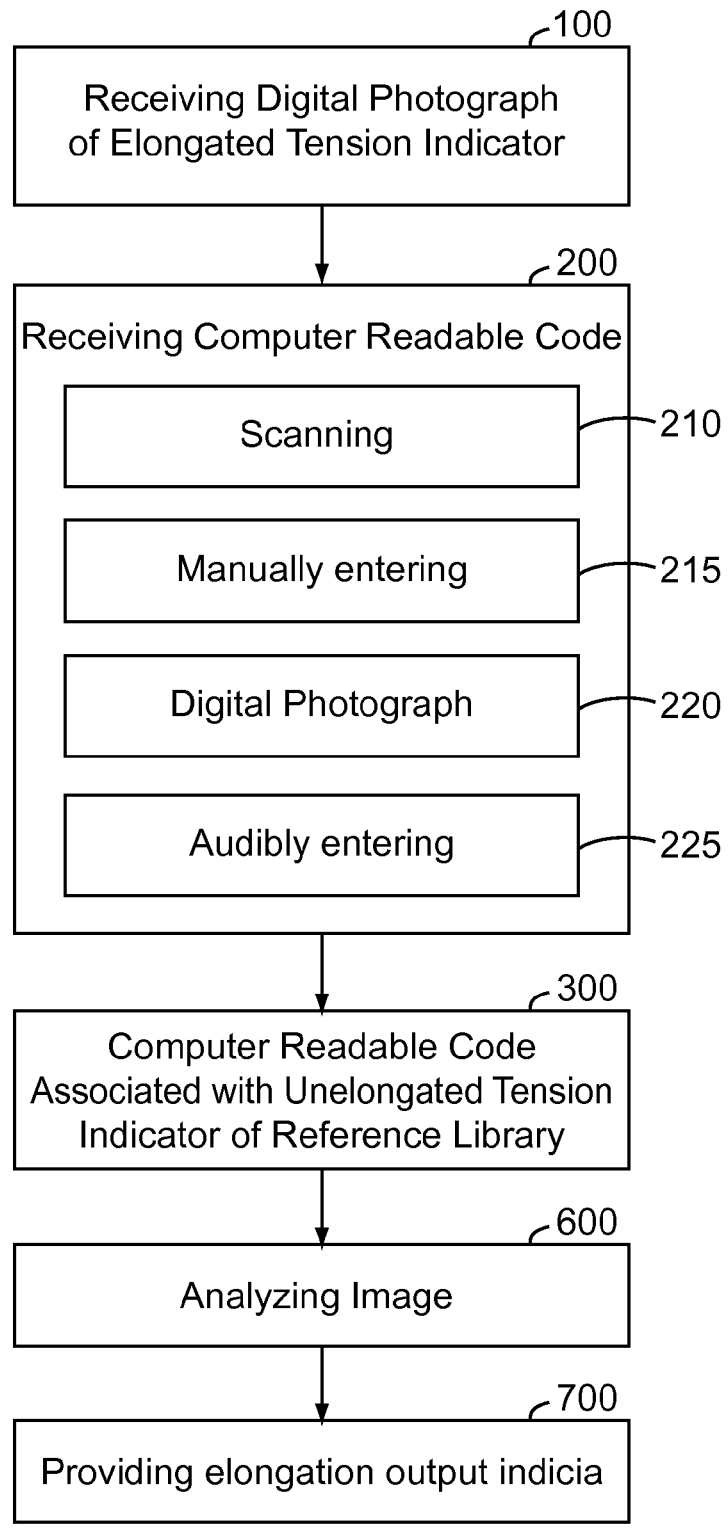
FIG. 6 is a flow chart of another embodied method of determining elongation of an elastic bandage by utilizing a computer readable code associated with the unelongated tension indicator (e.g. of a reference library)
Figure 7:
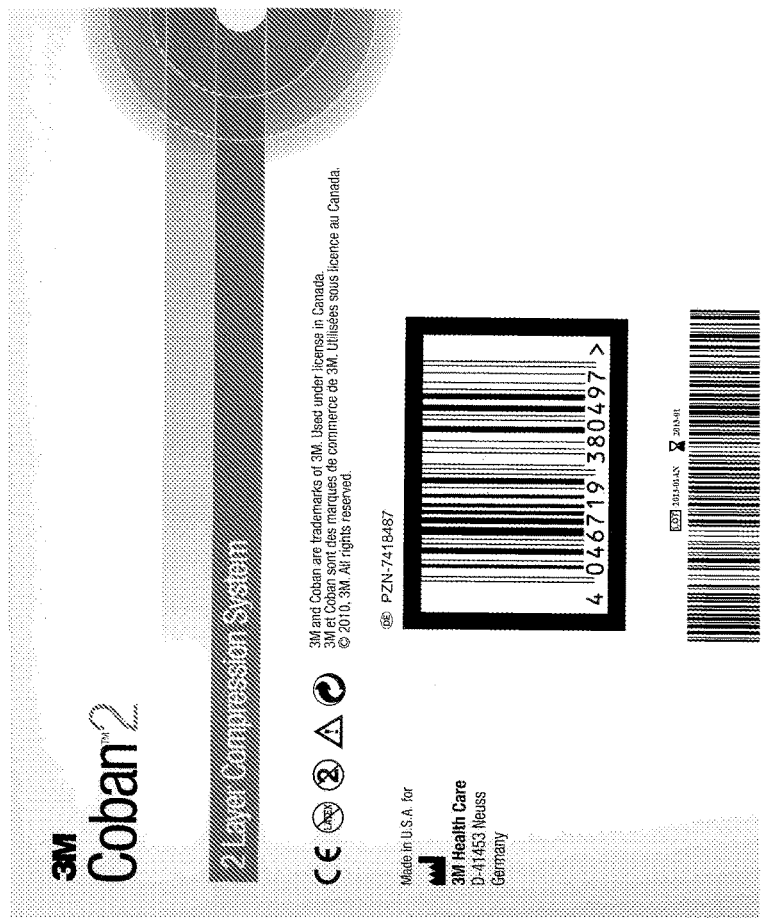
FIG. 7 is a computer readable UPC code associated with an elastic bandage.

With reference to FIG. 6, in yet another embodiment, the predetermined (e.g. unelongated) elongation state is associated with a computer readable code of a reference library 300. This embodiment is particularly useful when the computer program is intended to analyze the image date of a wide variety of elastic bandages from different manufacturers having different types of tension indicators. This embodiment comprises receiving a computer readable code 200, such as a UPC code (See FIG. 7). The computer readable code may be present on the elastic bandage product packaging, product literature, or even printed on the elastic bandage. The computer readable code can be provided by various means including scanning 210 the code or taking a digital photograph 220 of the code concurrently or separately than the digital photograph of the elongated or unelongated tension indicator. The computer readable code can also be provided by manually entering 215 the code as well as by audio input 225 such as by reciting the code to an audio recognition program. The computer code is associated with the predetermined (e.g. unelongated) elongation state of the tension indicator from the reference library, which is then utilized to determine the elongation of the elastic bandage. In some embodiments, the predetermined (e.g. unelongated) elongation state is stored by a remote server. In such embodiment, the analysis may also be conducted by the remote server. In other embodiments, the predetermined (e.g. unelongated) elongation state is downloaded from a remote server to the Smartphone computer application and the analysis is conducted by the Smartphone computer application.

A computer-implemented method of detecting elongation of an elastic bandage can reduce or eliminate human error.

For example, there is some subjectivity or a judgement call as to exactly when the figures of a tension indicator have been properly elongated, e.g. "when the large boxes of FIG. 1 become a square". If the boxes are less than a square, the tension may be too low. Likewise if the boxes are over extended, the tension can be too high. Another advantage is that such method can provide immediate verification as to whether the bandage has been applied correctly. Verification is particularly advantageous for in-home health care when the compression bandage may be self-applied or applied by a caregiver who is not a trained health care professional.

Although a computer-implemented method of detecting elongation of an elastic bandage is advantageous, in favored embodiments the method further comprises analyzing the image to determine the elongation and determining the tensile of the applied bandage. Determining the tensile is also an intermediate step in utilizing the Laplace equation to calculate the applied pressure of the elastic bandage.

Figure 8:
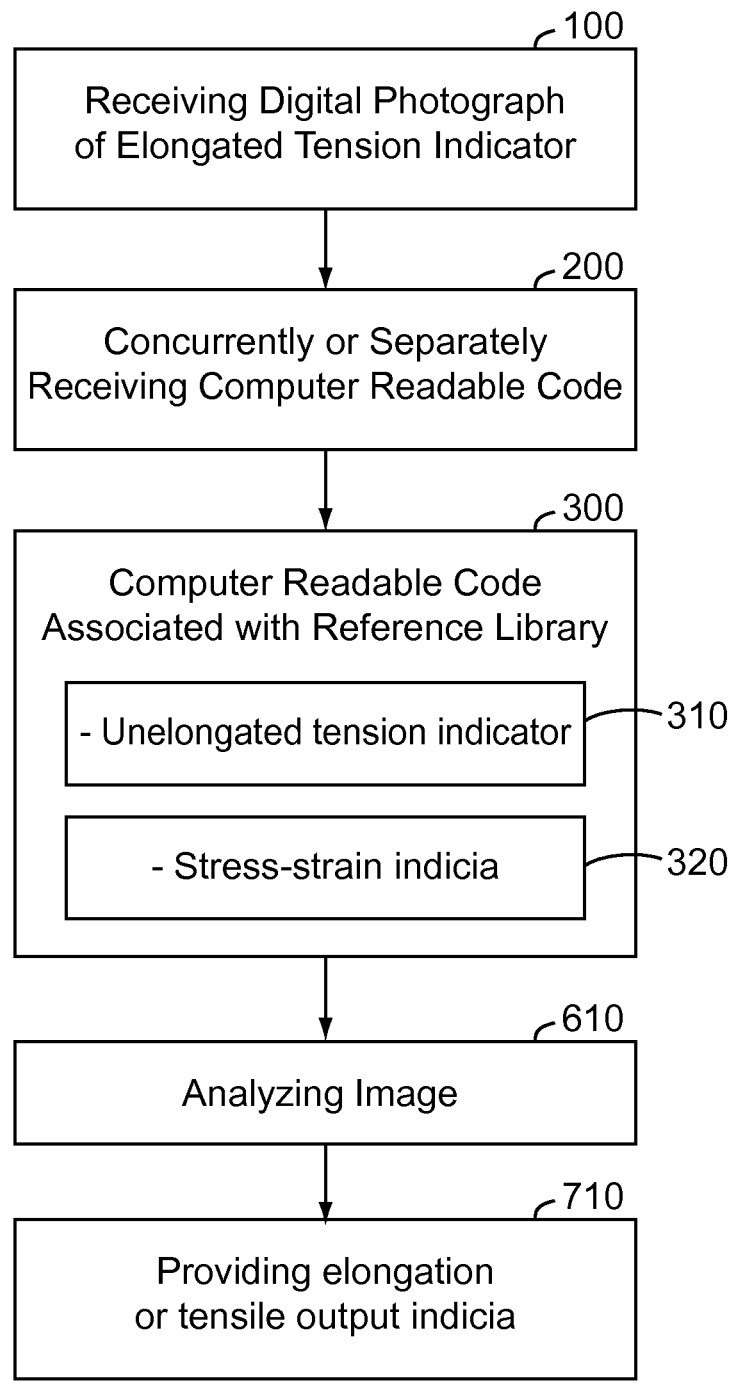
FIG. 8 is a flow chart of an embodied method of determining tensile of an elastic bandage.

With reference to FIG. 8, in another embodiment the method generally comprises receiving image data that includes a digital photograph of an elongated tension indicator of an elastic bandage 100, analyzing the image data to determine elongation of the elastic bandage 200 by comparing geometric features of the elongated tension indicator to model geometric features that define a predetermined elongation state, utilizing the determined elongation of the elastic bandage and stress-strain indicia to determine the tensile of the applied bandage 610; and providing output indicia associated with the tensile of the applied bandage 710. The output indicia can be displayed by the graphical interface or can be audio indicia, as previously described.

Figure 9:
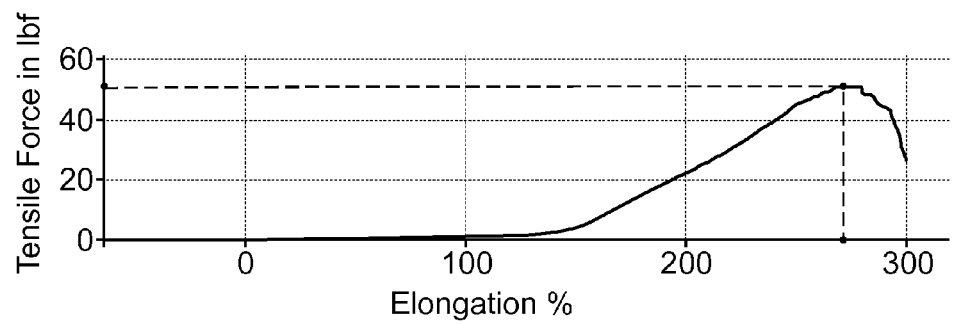
FIG. 9 depicts an illustrative stress-strain curve.

FIG. 9 depicts an illustrative stress-strain curve of an elastic bandage. The x-axis strain is equivalent to elongation; whereas the y-axis is tensile force. In this particular example, there is a linear relationship between the tensile force and the strain (i.e. elongation) for elongations ranging from about 160% to about 260%. Hence the tensile force can be computed from a simple linear equation from the determined elongation, provided that the elastic bandage has been elongated in the linear range. For other elastic bandages the relationship may not be linear. However, most any function can be deduced to a mathematical equation. Alternatively, the tensile can be obtained directly from the stress-strain curve.

In one embodiment, both the predetermined elongation state and the stress-strain indicia are preloaded and stored in the computer program of the Smartphone application or remote server. Thus the computer program determines (e.g. computes) the tensile of the applied elastic bandage from the elongation of the elastic bandage derived from analyzing the digital photograph of the elongated tension indicator and the stress-strain indicia.

In another embodiment, as depicted in FIG. 8, the predetermined elongation state 310 and stress-strain indicia 320 are associated with a computer readable code of a reference library 300, as previously described with respect to FIG. 6.

The Laplace equation concerns the relationship of various variables with regard to applied pressure. The Laplace equation, used to predict sub-bandage pressure, is derived from a formula described independently by Thomas Young (1773-1829) and by Pierre Simon de Laplace (1749-1827) in 1805. This defines the relationship between the pressure gradient across a closed elastic membrane and the tension in the membrane or film.

$$P_\alpha - P_\beta = \frac{2\gamma}{r}$$

In this formula $P\alpha$ and $P\beta$ are respectively the internal and external pressures at the surface, r is the radius of curvature, and $\gamma$ is the tension in the film. This equation indicates that the pressure inside a spherical surface is always greater than the pressure outside, but that the difference decreases to zero as the radius becomes infinite (when the surface is flat). In contrast, the pressure difference increases as the radius decrease and thus approaches infinity as r approaches zero. However, in practice the radius is significantly greater than zero.

In 1997, the Laplace equation was converted into following formula:

$$P=(TN\times4630)/CW$$

P=pressure measured in mmHg
T=tension of bandage measured in kgf
C=circumference of the limb measured in cm
W=width of bandage measured in cm
From Thomas (1997)

As evident by the Laplace equation, tension (which is a function of both elongation of the bandage and the stress-strain properties of the elastic bandage material) is a major factor related to applied pressure. However, the other factors (i.e. N, C, & W) are clearly disregarded when tension indicators alone are utilized to approximate applied pressure.

Figure 10:
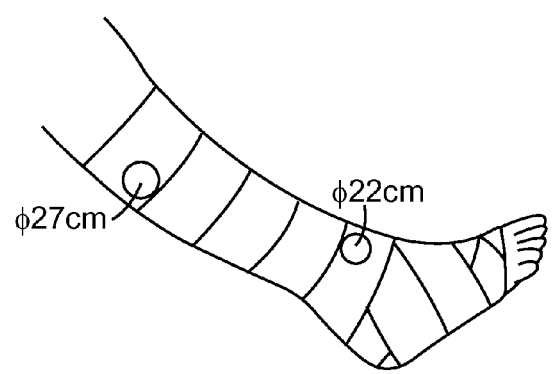
FIG. 10 depicts an elastic bandage applied to a three-dimensional member.

As illustrated in FIG. 10, the circumference of a three-dimensional member, such as a limb, can vary widely based on the particular location (e.g. ankle—22 cm, calf—27 cm, thigh—33 cm (not shown). The following table are calculations of applied pressure at various circumferences when the tensile force (i.e. elongation of the bandage) and number of layers is maintained constant.

| Pressure (P) (mmHg) | Tensile Force (T) (kg · f) | Layers (N) | Circumference (C) (cm) | Width (W) (cm) |
|---|---|---|---|---|
| 21 | 1.5 | 1 | 33 | 10 |
| 26 | 1.5 | 1 | 27 | 10 |
| 32 | 1.5 | 1 | 22 | 10 |

As evident by the above table, the applied pressure at the ankle is 32 mm of mercury, yet the applied pressure at the thigh is 21 mm of mercury (Hg).

During compression therapy it is common to spirally wind the bandage about a three-dimensional member (e.g. limb), such that adjacent laps of the bandage overlap (e.g. 50 to 70%). However, variation in applied pressure is further exasperated when the number of layers is taken into consideration, as evident by the following table.

| Pressure (P) (mmHg) | Tensile Force (T) (Kg · f) | Layers (N) | Circumference (C) (cm) | Width (W) (cm) |
|---|---|---|---|---|
| 21 | 1.5 | 1 | 33 | 10 |
| 26 | 1.5 | 1 | 27 | 10 |
| 32 | 1.5 | 1 | 22 | 10 |
| 42 | 1.5 | 2 | 33 | 10 |
| 51 | 1.5 | 2 | 27 | 10 |
| 63 | 1.5 | 2 | 22 | 10 |
| 63 | 1.5 | 3 | 33 | 10 |
| 77 | 1.5 | 3 | 27 | 10 |
| 95 | 1.5 | 3 | 22 | 10 |

-continued

| Pressure (P) (mmHg) | Tensile Force (T) (Kg · f) | Layers (N) | Circumference (C) (cm) | Width (W) (cm) |
|---|---|---|---|---|
| 84 | 1.5 | 2 | 33 | 5 |
| 100 | 1.5 | 2 | 27 | 5 |
| 126 | 1.5 | 2 | 22 | 5 |

Thus, it is evident from the tables above the utilizing tension indicators alone does not provide a very accurate approximation of applied pressure.

Figure 11:
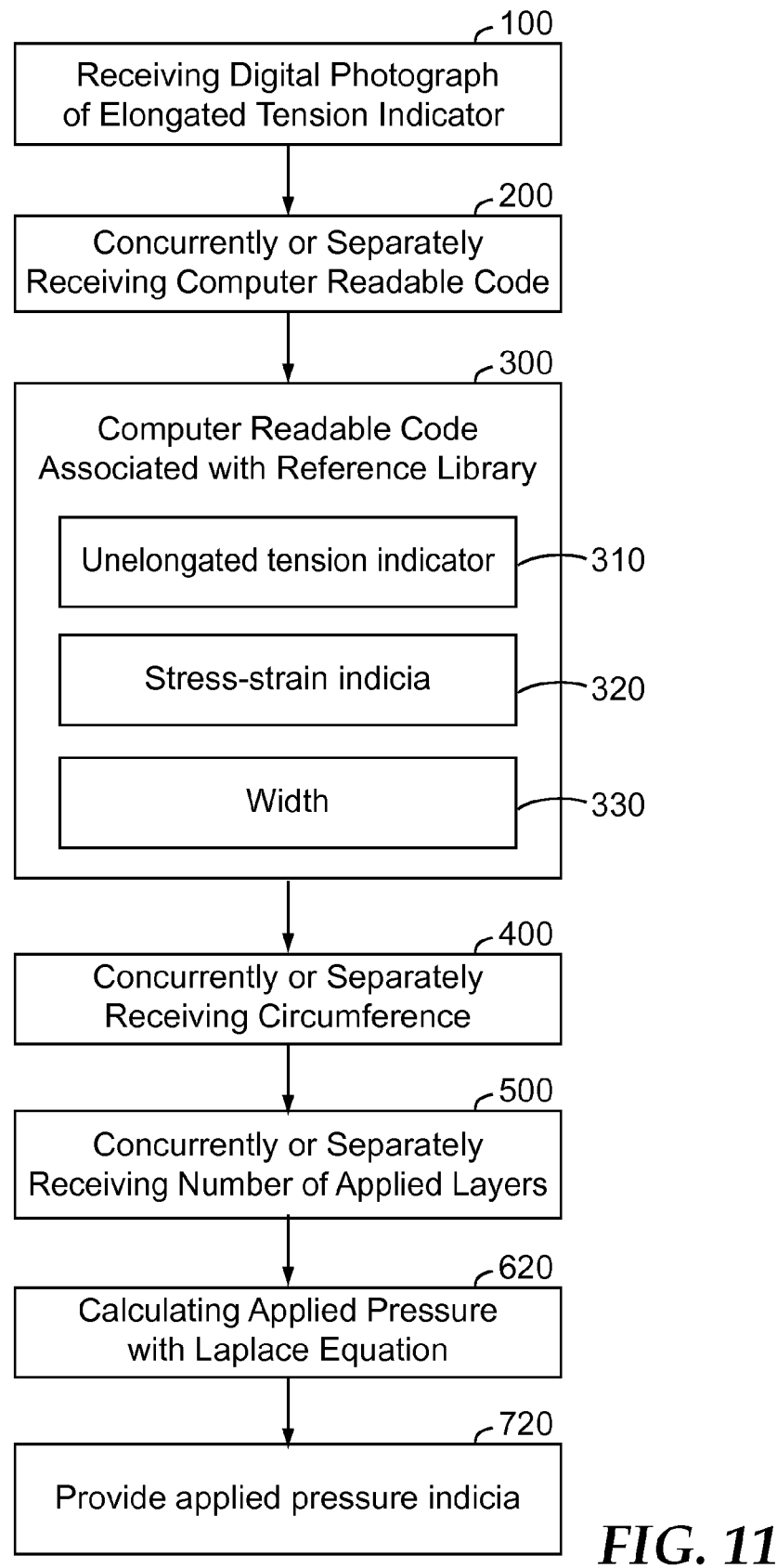
FIG. 11 is a flow chart of an embodied method of determining applied pressure of an elastic bandage.

With reference to FIG. 11, in another embodiment, a computer-implemented method of detecting applied pressure of an elastic bandage is described comprising receiving image data that includes a digital photograph of an elongated tension indicator 100 of an elastic bandage; utilizing the Laplace equation to determine the applied pressure 620; and providing indicia associated with applied pressure 720. The tension (T) is determined from the elongation and stress-strain indicia, as previously described with respect to FIG. 8. The predetermined elongation state 310 and stress-strain indicia 320 can be associated with a computer readable code of a reference library 300. The width 330 of the elastic bandage may also be associated with the computer readable code. The circumference 400 of the three-dimensional member (to which the elastic bandage is applied) and the number of applied layers 500 may be separately received. When more than one overlapping layer is applied, typically the computer program will prompt the user to enter the number of layers applied and the percentage of overlap of each layer. The computer program may also prompt the user to also enter the circumference of the three-dimensional member (e.g. limb). However, the circumference the number of applied layer may also be concurrently received from analysis of the digital photograph. For example, the circumference at various locations can be approximated from the digital photograph assuming a cylindrical shaped member (having a small height). Further, when only a single overlapping layer is applied, the number of layers can also be determined from analysis of a digital photograph. The digital photograph of the elongated tension indicator is typically a close-up such as depicted in FIG. 4. Thus a second photograph of the entire elastic bandage wrapped member may be received for the purpose of determining the number of layers applied.

In some embodiments, the methods described herein utilize a computer readable code for the purpose of accessing information associated with the elastic bandage such as the predetermined (e.g. unelongated) elongation state of the tension indicator, stress-strain indicia, or width of the bandage. The computer readable code may be present on the elastic bandage itself or a package thereof. The computer readable code can be applied with conventional printing processes such as offset printing, flexoprinting, or gravure printing, but also with laser printing, thermodirect, thermotransfer, or inkjet printing. In a hospital setting the elastic bandages may be provided in a cart having bins of various elastic bandages with the code provided on the bin or on a (e.g. laminated) card accompanying the cart. Scanning or photographing a computer readable code on the bandage itself or individual package thereof can be amenable to reducing errors such as improperly entering the wrong UPC number or inadvertently scanning the wrong code. It has been found that computer readable (e.g. UPC bar) code can be read by an HTC EVO Android barcode scanner even when elongated 300% (i.e. 4 times the unstretched length). Thus, an elongated computer readable code can currently be received with the elongated tension indicator.

Various computer readable codes are known including for example data-matrix codes, maxi-codes, Aztec codes, and dot-codes/point codes. In some embodiments, the code is a one-dimensional code, commonly known as bar codes or UPC code, such as exemplified in FIG. 7. Alternatively the code may be a two-dimensional code such as a QR code. Both one-dimensional and two-dimensional codes can be read with optical reading devices, such as for example barcode reading devices (scanners) or (CCD) digital cameras of mobile computing devices such as Smartphones.

Barcodes such as UPC codes are generally considered one-dimensional codes, i.e. a code applied in a single axis (e.g. x-axis). Two-dimensional codes, such as QR codes are applied in two axes. These codes can consist of stacked one-dimensional codes, arranged in lines, or true aerial codes. In addition, so-called 3D-codes exist, with the tone of color, color saturation, or brightness representing the third dimension, for example. Two-dimensional codes typically encode information perpendicular to a first axis direction (e.g. x-axis and y-axis).

The code can cover an area of a minimum of 0.5 cm². A typical size of a UPC bar code or two dimensional code is about 20 to 25 cm². However, the code may be larger if desired, ranging in size up to 50 or even 100 cm².

True aerial codes or matrix codes, also called array codes, can be differentiated from stacked codes. In matrix codes, data is encoded evenly within a matrix of blocks. The direction is irrelevant, so that reading is possible omnidirectionally. This is advantageous as it simplifies reading by the scanner or digital camera. Two-dimensional matrix codes (e.g. QR codes) can be very small, and possess nearly unlimited durability. Data provided in a QR code is typically redundant. Depending on design, data can still be decoded even if up to 30% of the code is missing or destroyed.

Many of today's mobile phones or tablet computers with a built-in camera include software allowing the reading of bar codes and QR codes. The code can encode a specific internet or web address automatically leading to the respective encoded internet site. In addition to utilizing the code for the purpose of accessing information associated with the elongation or applied pressure analysis of the elastic bandage, the code may be also utilized to provide a link to the computer application or computer program of a remote server. Further, other relevant information for the elastic bandage can be obtained immediately from this internet site, while avoiding generally searching the internet or searching the homepage of the manufacturer.

The tension indicator may comprise the computer readable code. For example, a rectangular shaped unelongated tension indicator comprising a bar code or two-dimensional code that can be stretched to a square is an example of a tension indicator comprising a computer readable code. As previously described, bar codes are recognizable as being the same code even when stretched. In the case of two-dimensional codes, it may be necessary to associate both the unelongated code and various elongated states of the code with the same elastic bandage product.

Figure 12:
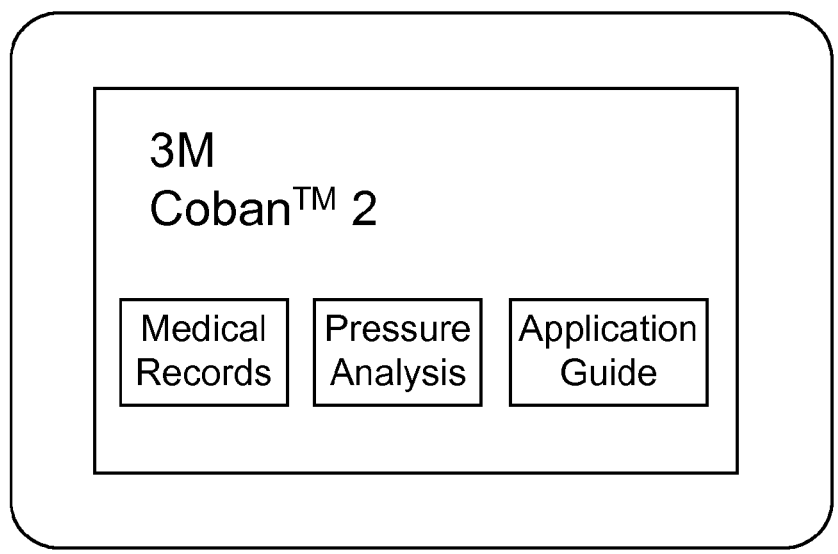
FIG. 12 depicts other information that can be accessed with the computer readable code associated with the elastic bandage.

The elastic bandage can be associated with more than one computer readable code. For example, one code may be associated with the predetermined (e.g. unelongated) elongation state and another code for may be associated with stress-strain indicia. However, in a favored embodiment a single code automatically leads to a single encoded internet site (See FIG. 12) that provides a menu of options including the elongation and/or applied pressure analysis option. This single menu can also provide other options or links such as an elastic bandage application guide, a link to a medical record, a link to an elastic bandage sales representative, a link to an elastic bandage supplier, or a direct connection to a consultation site or hotline for the elastic bandage. It is preferred that the internet site provides the information or data in the language of the country where the product was sold. This information can be added to the code as additional information so that the consumer will be directed immediately to the internet site in the respective language or the single menu can provide a language selection.

Figure 13:
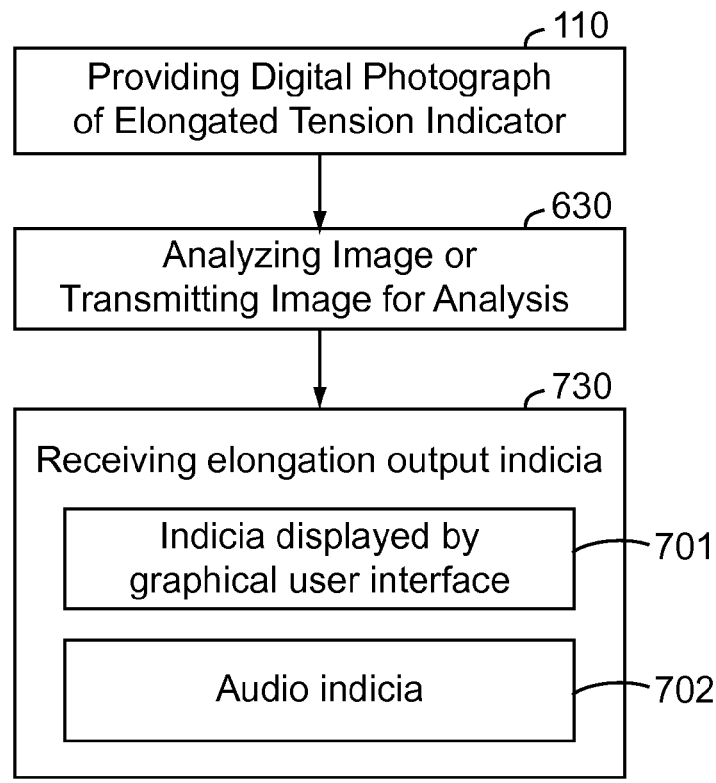
FIG. 13 is a flow chart of an embodied method of determining elongation of an elastic bandage with respect to the steps conducted by the user of the method.

In other embodiments, the various methods of detecting elongation, tension, applied pressure etc. can be described with respect to the steps conducted by the user of such computer-implemented method, i.e. whereas the steps of receiving and providing are interchanged. The user may be a healthcare practitioner that is applying or verifying the application of a compression bandage. The user may also be a patient or caregiver that is not a healthcare professional. For example, with reference to FIG. 13 in one embodiment, a computer-implemented method of detecting elongation of an elastic bandage is described comprising providing image data that includes a digital photograph of an elongated tension indicator 110 of an elastic bandage; analyzing the image data or transmitting (e.g. uploading) the image data for analysis 630 to determine the elongation of the elastic bandage by comparing geometric features of the elongated tension indicator to model geometric features that define a predetermined elongation state; and receiving output indicia 730 associated with the determined elongation. The output indicia may be displayed by the graphical interface 701 or may be audio indicia 703, as previously described.

Figure 14:
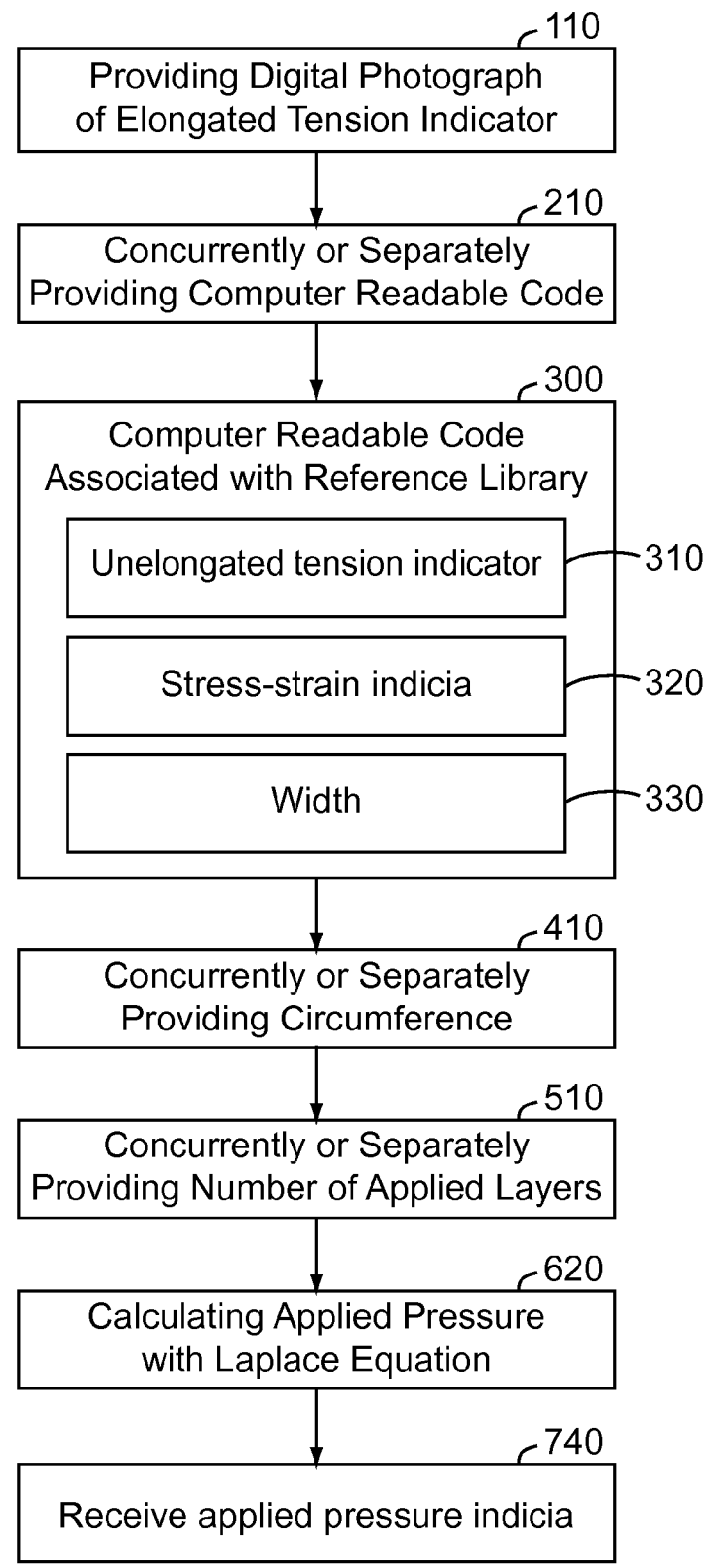
FIG. 14 is a flow chart of an embodied method of determining applied pressure of an elastic bandage with respect to the steps conducted by the user of the method.

With reference to FIG. 14, in yet another embodiment a computer-implemented method of detecting applied pressure of an elastic bandage is described comprising providing image data that includes a digital photograph of an elongated tension indicator 110 of an elastic bandage; utilizing the Laplace equation to determine the applied pressure 620; and receiving indicia associated with applied pressure 740. The tension (T) is determined from the elongation and stress-strain indicia, as previously described with respect to FIG. 8. The predetermined elongation state 310 and stress-strain indicia 320 are associated with a computer readable code of a reference library 300. The width 330 of the elastic bandage may also be associated with the computer readable code. The circumference 410 of the three-dimensional member (to which the elastic bandage is applied) and the number of applied layers 510 may be separately received, as also previously described.

Figure 15:
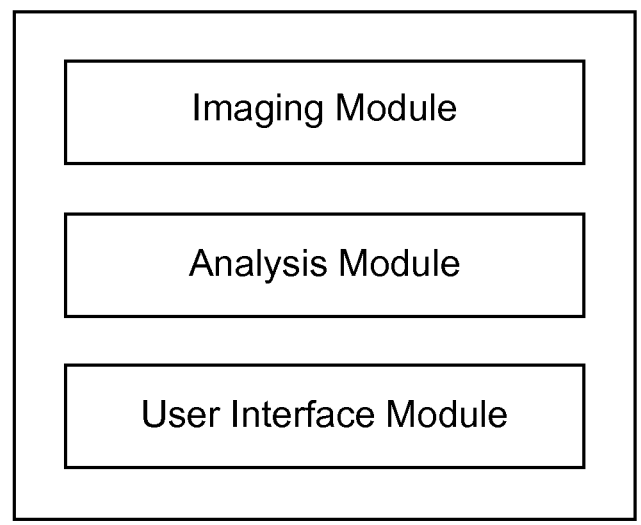
FIG. 15 depicts a computer-implemented system.

With reference to FIG. 15, also described is a computer-implemented system. A mobile-computing device may comprise such system or such system may reside on a remote server. In either embodiment, the computer implemented system comprises an image module. The image module is capable of receiving indicia indicative of a digital photograph of an elongated tension indicator of an elastic bandage. The computer-implemented system further comprises an analysis module. The analysis module is capable comparing geometric features of the elongated tension indicator to model geometric features that define a predetermined elongation state. In some embodiments, the analysis module is capable of determining the tension of the elongated bandage by use of the determined elongation and stress-strain indicia. In yet other embodiments, the analysis module is further capable of calculating the applied pressure of the elongated bandage by utilizing the Laplace equation. The computer-implemented system is further comprises a user interface module capable of providing output graphical or audio indicia associated with the determined elongation, tension, and/or applied pressure. The user interface module may also prompt the input of various information for use by the analysis module such as the digital photograph, computer readable code, circumference of the three-dimensional member to which the elastic bandage is applied, the number of layers applied, etc.

The new method and systems described herein produce various (e.g. intermediate) articles. In some embodiments, the article is non-transient computer readable medium comprising indicia indicative of a digital photograph of an elongated tension indicator of an elastic bandage and a computer readable code. The computer readable code is associated with the unelongated tension indicator, stress-strain indicia of the elastic bandage, width of the elastic bandage, an elastic bandage application guide, a link to a medical record, a link to an elastic bandage sales representative, a link to an elastic bandage supplier, or a direct connection to an elastic bandage consultation site; as well as any combination of such information. The computer readable code may be a bar code or a two-dimensional matrix code. Such code may be contained within or integrated with the tension indicator.

In another embodiment, a three-dimensional member (e.g. limb) is described comprising at least one layer of an elastic bandage wherein the applied layer comprises an elongated tension indicator and a computer readable code. The computer readable code is associated with various information as just described.

The present invention is applicable to a wide variety of elastic bandages. Each bandage is sufficiently elastic such that it is capable of being wound 2 or more turns (more suitably 5 or more turns) about a limb of a patient.

The particular dimensions of the bandages depend in part on the particular limb being treated and/or the particular patient. For example, in human (adult) therapy for use with lower limbs, suitable dimensions for the bandages may be about 70 to about 130 mm wide and about 2 to about 4.5 m long, while for use with upper limbs a width of about 70 to about 130 mm is suitable with a corresponding shorter length than that use for lower limbs. For applications in veterinary medicine, depending on the particular animal patient, appropriate, suitable dimensions may be larger (e.g., for equine bandaging) or smaller (e.g., for canine bandaging).

Bandages are generally sufficiently porous to allow for transmission of air and moisture vapor through the bandage (e.g., a water vapor transmission rate (WVTR) of at least 240 g/m$^2$/24 h, more suitably of at least 400 g/m$^2$/24 h, e.g., as determined by ASTM E398-03 at 37.8.degree. C. and 100% relative humidity in the wet chamber and 37.8 degrees C. and 10% relative humidity in the dry chamber). In addition, each bandage, in particular the inner skin-facing bandage, may be sterilized, e.g., gamma sterilized.

Elastic bandage generally provide a compressive force when extended ranging from about 1 to about 80 mm Hg (more suitably from about 20 to about 75 mmHg, most suitably from about 30 to about 70 mmHg) (e.g. at a position 8 cm above the medial malleolus, when wrapped about a human adult leg with an ankle circumference of 22 cm).

Elastic bandage may be classified as "long-stretch" elastic bandages, intended to be elongated greater than 100-120%. In some embodiments, such elastic bandages may be elongated up to 150%, 200%, 250%, 300%, 350% or 400%. In some embodiments, the elastic compression bandages may be classified as "short-stretch" elastic bandages, generally exhibiting a relatively low extensibility in its longitudinal direction, in particular having a stretch capability in the longitudinal direction of not more than 75%, or 65%, or 60% or 55%, e.g., as determined in accordance with the Stretch Testing Procedure described in U.S. Pat. No. 7,852,716; incorporated herein by reference. The stretch capability is typically at least 20%, 25%, or 30% in the longitudinal direction. Further, the recovery-of-stretch capability is typically at least 85%, or 90%, or 95%.

Preferred outer-facing (as opposed to skin facing) surfaces of bandages do not adhere to clothing, hair or skin. Outer-facing surface of bandages are typically self-adhering elastomeric bandages. Examples of suitable types of self-adherent elastomeric bandages as well as methods of making such bandages are disclosed in U.S. Pat. Nos. 3,575,782; 4,984,584; US Published Application No. 2005/0025937A, and U.S. Pat. No. 6,156,424. Commercially available self-adhering elastomeric bandage are available under the trade designations ROSIDAL HAFT (Lohman & Rauscher GmbH & Co. KG, Neuwied Germany) and ACTICO (Activa Health Care, Burton-upon-Trent, UK).

Elastic bandages may suitably comprise a woven, knitted or nonwoven bandage comprising generally a plurality of generally longitudinally extending elastic yarns in the woven, knitted or nonwoven structure, the bandage being coated or impregnated with a polymer binder. More suitably outer bandages may comprise a plurality of generally longitudinally extending, (preferably partially extended) elastic yarns bound with a polymeric binder between two webs or bound with a polymeric binder on a web. The polymeric binder is cohesive, so that the bandage is self-adherent (i.e. in use the bandage will remain adhered to itself under elastic extension e.g., without the use of a fastening mechanism.

Suitable polymeric binders may comprise natural rubber latex, a synthetic latex, such as homopolymer and copolymer latexes of acrylics, butadienes, styrene/butadiene rubbers, chloroprenes, ethylenes (e.g., vinyl acetate/ethylene), isoprenes, nitriles and urethanes, or mixtures thereof. In some embodiments, outer bandages are free of natural rubber latex.

Extent of compression provided is generally related to, inter alia, size of the elastic yarns and the number of yarns, whereby increased compression is typically a result of using greater number of larger elastic yarns in the bandage. The number of elastic yarns per inch (epi) of the bandage may range from about 8, 9, or 10 to about 20 or 25 epi, while the elastic yarns may have a denier ranging from about 300, 400, or 500 denier to about 1500 denier, and typically no greater than 650 or 600 denier.

In some embodiments, the bandage comprises an inner skin facing, elongated, elastic bandage 10 and an outer, elongated, self-adhering, elastic compression bandage 20.

The number of elastic yarns per inch (epi) of the inner bandage is typically no greater than 15, 14, 13, 12, 11, or 10 epi or less. Within this range, an epi of 4, 6, or 6 can be favored. The elastic yarns of the inner bandage are typically no greater than 550, 450 or 350 denier or less and at least 100, 150, or 200 denier.

As shown in U.S. Pat. No. 7,854,716; incorporated herein by reference, in one embodiment the inner bandage comprises a foam layer affixed to the first face of the elastic substrate. A variety of means are suitable for affixing the foam layer onto the elastic substrate such as stitching, needle tacking, ultrasonic welding or bonding, e.g., mechanical, thermal, and chemical bonding as well as combinations thereof. Suitable means of chemical bonding include using an adhesive, for example in the form of a continuous or discontinuous layer (e.g., a pattern-coated adhesive layer), as further described in previously cited U.S. Pat. No. 7,854, 716. Flexible, resilient, polymeric foams containing open cells are preferred. Suitable foams include, but are not limited to, polyurethane, carboxylated butadiene-sytrene rubber, polyester, polyacrylate, polyether, and polyolefin foams. Foams used for the foam layers are typically absorbent foams, e.g., absorbing greater than 250% aqueous saline solution when immersed for 30 minutes in phosphate saline containing 0.9 wt % NaCl at 37 degrees C. The average cell size (typically, the longest dimension of a cell, such as the diameter) of the foam is typically at least about 30 or 50 microns and no greater than about 800, 700, 600, or 500 microns, as measured by scanning electron microscopy (SEM) or light microscopy. Suitable foams may be either hydrophilic or hydrophobic, more suitably they may be hydrophobic and treated to render them more hydrophilic, e.g., with surfactants such as nonionic surfactants, such as oxypropylene-oxyethylene block copolymers.

In one favored embodiment, the compression bandage comprises: a) an inner skin facing, elongated, elastic bandage having inner and outer faces and comprising: (i) an elongated, elastic substrate having first and second faces, the second face comprising a self-adhering material, and (ii) an elongated layer of foam, said foam layer being affixed to the first face of said substrate and extending 33% or more across said first face of substrate in transverse direction and 67% or more across said first face of substrate in longitudinal direction. The foam layer having an exposed face is not affixed to the first face of said substrate and does not comprise a self-adhering material. The inner face of the inner bandage comprises the exposed face of the foam layer, and the outer face of the inner bandage comprises the second face of the elongated, elastic substrate. The bandage further comprises an outer, elongated, self-adhering elastic bandage; having a compressive force when extended. The outer bandage overlies the inner bandage, and said inner face of the inner bandage faces the skin, and the outer face of the inner bandage faces said outer bandage. The inner and outer bandages are configured such that in use the bandages remain adhered to one another under elastic extension without the use of a fastening mechanism and is free of any additional elongated bandages.

The following example further illustrates the practice of the invention:

An elastic compression bandage having a width of about 4 inches may be printed with the previously described tension indicator of FIG. 2. This tension indicator may be printed with conventional printing methods at regular intervals throughout the length of the wrap.

During application to a limb, the practitioner may utilize the colored bars of the tension indicator as a guide for stretching of the elastic bandage. In this case, 50% stretch is indicated when the green segment is observed as a square; 100% stretch when the blue segment is indicated a square; 200% stretch when the red segment is a square; 300% stretch when the black segments are observed as a square. When the wrapping process is complete, the practitioner may first scan the UPC from the elastic bandage package (e.g. FIG. 7) which will automatically link the practitioner to an elongation or pressure analysis web link. Alternatively, the practitioner may download such computer application onto their Smartphone. The program will prompt the user to take a digital photograph of the elongated tension indicator. The program may also prompt the user to take a digital photograph of the unelongated tension indicator or such information is preprogrammed or associated with the scanned UPC code. The program mathematically calculate the difference in dimensions between the elongated an unelongated tension indicators and provides a positive or negative indication as to whether the elastic bandage has been elongated to within the proper range.

What is claimed is:

1. A computer-implemented system having a processor and a graphical user interface comprising:
    an image module capable of receiving indicia indicative of a digital photograph of an elongated tension indicator of an elastic bandage, wherein the elastic bandage comprises an overlap guide in addition to the tension indicator, and wherein the elastic bandage is spirally wound about a three-dimensional member;
    an analysis module capable of:
        comparing geometric features of the elongated tension indicator to model geometric features that define a predetermined elongation state;
        determining the tension of the elongated bandage by use of a determined elongation and stress-strain indicia;
        calculating the applied pressure of the elongated bandage by utilizing an equation, wherein the equation is the Laplace equation; and
    a user interface module capable of providing output indicia associated with the determined elongation, wherein the output indicia is a representation of applied pressure of the bandage.

2. The computer-implemented system of claim 1, wherein comparing geometric features comprises:
    accessing a computer readable code stored on a mobile computing device, wherein the computer readable code is associated with the predetermined elongation state of the elastic bandage, wherein the computer readable code is readable with an optical reading device.

3. The computer-implemented system of claim 1 further comprising:
    a reference library stored on the computer-implemented system.

4. The computer-implemented system of claim 3 wherein the reference library further comprises stress-strain indicia associated with the elastic bandage.

5. The computer-implemented system of claim 4 wherein the reference library further comprises additional information associated with computer readable code selected from an elastic bandage application guide, a link to a medical record, a link to an elastic bandage sales representative, or a link to an elastic bandage supplier, or a direct connection to an elastic bandage consultation site.

6. The computer-implemented system of claim 1 wherein the analysis module is capable of determining the number of applied layers of the elastic bandage on the three-dimensional member from a second digital photograph.

7. The computer-implemented system of claim 6 wherein the elastic bandage has a length and a width, wherein the elastic bandage has a continuous or intermittent marking in a central portion relative to the width of the elastic bandage that is parallel to the length of the elastic bandage, wherein the determining the number of applied layers comprises determining the number of applied layers based on the marking on the elastic bandage.

8. The computer-implemented system of claim 6 wherein the number of applied layers is determined by the summation of each layer multiplied by a fraction of the extent of overlap.

9. The computer-implemented system of claim 1 wherein the calculating the applied pressure utilizes the following Laplace equation:

$$\text{Applied Pressure(mmHg)} = (TN \times 4630)/CW$$

wherein T is tension in kgf, N is number of applied layers, C is circumference in cm, and W is width of the bandage in cm.

10. The computer-implemented system of claim 1 wherein the enlongated tension indicator comprises a computer readable code and the code can be read from the digital photograph.

11. The computer-implemented system of claim 1 wherein the analysis module is capable of determining the width of the elastic bandage from indicia indicative of the digital photograph.

12. The computer-implemented system of claim 1 wherein the analysis module is capable of determining the circumference of the three-dimensional member from indicia indicative of the digital photograph.

13. A system comprising:
    the computer-implemented system of claim 1;
    an elastic bandage having a tension indicator and an overlap guide; and
    a three-dimensional member, wherein the elastic bandage is spirally wound about the three-dimensional member.

14. The system of claim 13, wherein the elastic bandage has a length and a width, and wherein the overlap guide comprises a continuous or intermittent marking in a central portion of the elastic bandage relative to the width of the elastic bandage that is parallel to the length of the elastic bandage.

15. The system of claim 14, wherein the analysis module is capable of determining the number of applied layers based on the marking on the elastic bandage.

16. The system of claim 13, wherein the tension indicator comprises a repeating pattern of a set of geometric tension indicators, wherein a repeat interval of the repeating pattern is no greater than half the circumference of the three-dimensional member.

17. The system of claim 16, wherein the repeat interval is no greater than 10 cm.

18. The system of claim 13, wherein the elastic bandage is 70 mm to 130 mm wide.

19. The system of claim 13, wherein the elastic bandage provides a compressive force from 1 mmHg to 80 mmHg when wound about the three-dimensional member.

* * * * *

UNITED STATES PATENT AND TRADEMARK OFFICE
CERTIFICATE OF CORRECTION

PATENT NO.        : 9,798,930 B2
APPLICATION NO.   : 14/406812
DATED             : October 24, 2017
INVENTOR(S)       : Junkang Liu Page 1 of 1

It is certified that error appears in the above-identified patent and that said Letters Patent is hereby corrected as shown below:

In the Specification

Column 1
Line 8, delete "PCT/US2013," and insert -- PCT/US2013/049220, --, therefor.

Column 2
Line 49, delete "stain" and insert -- strain --, therefor.

Column 4
Line 5, delete "elipses." and insert -- ellipses. --, therefor.
Line 37, delete "elipses" and insert -- ellipses --, therefor.

Column 12
Line 57, delete "80 mm Hg" and insert -- 80 mmHg --, therefor.

Column 14
Line 3, delete "resilent," and insert -- resilient, --, therefor.
Line 5, delete "-sytrene" and insert -- -styrene --, therefor.

In the Claims

Column 16
Line 19 Claim 10, delete "enlongated" and insert -- elongated --, therefor.

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*